US007387884B2

United States Patent
Suzuki et al.

(10) Patent No.: US 7,387,884 B2
(45) Date of Patent: Jun. 17, 2008

(54) YEAST EXTRACT SOLUTION FOR CELL-FREE PROTEIN SYNTHESIS, METHOD FOR PREPARATION THEREOF AND METHOD FOR CELL-FREE PROTEIN SYNTHESIS USING SAME

(75) Inventors: Takashi Suzuki, Osaka (JP); Toru Ezure, Osaka (JP); Masaaki Ito, Osaka (JP)

(73) Assignee: Shimadzu Corporation, Kyoto (JP)

( * ) Notice: Subject to any disclaimer, the term of this patent is extended or adjusted under 35 U.S.C. 154(b) by 291 days.

(21) Appl. No.: 10/751,962

(22) Filed: Jan. 7, 2004

(65) Prior Publication Data

US 2004/0137560 A1    Jul. 15, 2004

(30) Foreign Application Priority Data

Jan. 7, 2003    (JP)    ............... 2003-001317

(51) Int. Cl.
*C12P 21/06*    (2006.01)
(52) U.S. Cl. ..................................... 435/68.1
(58) Field of Classification Search ................ 435/68.1
See application file for complete search history.

(56) References Cited

U.S. PATENT DOCUMENTS

2002/0168705 A1    11/2002    Nunokawa et al. ........ 435/68.1
2003/0199076 A1    10/2003    Kuroita et al. ........... 435/252.8

FOREIGN PATENT DOCUMENTS

EP    1 176 210    1/2002

OTHER PUBLICATIONS

M. C. Schultz, "Cchromatin Assembly in Yeast Cell-Free Extracts", Methods, A Companion to Methods in Enzymology, vol. 17, No. 2, pp. 161-172, Feb. 1999.
E. Kobatake et al., "Translation of Immobilized Genetic Information by Yeast Cell-Free Protein Synthesizing System", Biotechnology and Bioengineering, vol. 37, pp. 723-728, 1991.
R. T. Lyons et al., "Effects of Fasting and Insulin Administration on Polyribosome Formation in Rat Epididymal Fat Cells", The Journal of Biological Chemistry, vol. 255, No. 13, pp. 6330-6334, Jul. 13, 1980.
I. Hussain et al., "Translation of Homologous and Heterologous Messenger RNAs in a Yeast Cell-Free System", Gene, vol. 46, 1986, pp. 13-23.
E. Gasior et al., "The Preparation and Characterization of a Cell-Free System from *Saccharomyces cerevisiae* that Translates Natural Messenger Ribonucleic Acid", The Journal of Biological Chemistry, vol. 254, No. 10, May 25, 1979, pp. 3965-3969.

*Primary Examiner*—Jon Weber
*Assistant Examiner*—Kailash C Srivastava
(74) *Attorney, Agent, or Firm*—Wenderoth, Lind & Ponack, L.L.P.

(57) ABSTRACT

The present invention provides a preparation method of a yeast extract solution for cell-free protein synthesis, which solution is easy to prepare and is capable of synthesizing a higher amount of a protein than by conventional yeast extract solutions, the yeast extract solution, a cell-free synthesis method of protein, which uses the yeast extract solution, and a kit for cell-free protein synthesis containing the yeast extract solution. The method of the present invention includes rupturing a yeast cell in a frozen state, and obtaining an extract thereof.

4 Claims, 3 Drawing Sheets

YEAST EXTRACT SOLUTION FOR CELL-FREE PROTEIN SYNTHESIS, METHOD FOR PREPARATION THEREOF AND METHOD FOR CELL-FREE PROTEIN SYNTHESIS USING SAME

This is a U.S. application that claims priority to Japanese application, JP 1317/2003, filed Jan. 7, 2003.

TECHNICAL FIELD OF THE INVENTION

The present invention relates to a yeast extract solution usable for cell-free protein synthesis, a preparation method thereof, a protein synthesis method in a cell-free system using the extract solution, and a kit for cell-free protein synthesis, which contains the yeast extract solution.

BACKGROUND OF THE INVENTION

In recent years, genetic information of many organisms, such as human genome, has been decoded. Under the circumstances, functional analysis of proteins and creation of genomic medicine based on such genetic information have been attracting attention for postgenomic studies. Application and utilization of proteins corresponding to such genetic information for pharmaceutical products and the like requires easy synthesis of extensive kinds of proteins in a short time.

At present, expression systems using viable cells (hereinafter sometimes to be referred to as "cell-system") of yeast, insect cell and the like by the gene recombination technique have been widely utilized as the production methods of proteins. However, viable cells show a propensity toward elimination of exogenous proteins for their functional retention, and there are many proteins that cannot be expressed easily since expression of cytotoxic proteins in viable cells prevents cell growth.

On the other hand, as a production method of protein free of a cell-system, cell-free protein synthesis has been known, which includes adding a substrate, an enzyme and the like to a cell rupture, extract solution and the like to provide a wide choice of genetic information translation systems of organisms in test tubes, and reconstructing a synthetic system capable of linking the necessary number of amino acid residues in a desired order using an mRNA encoding an object protein. Such a cell-free protein synthesis is relatively free of the limitation imposed on the above-mentioned cell-system protein synthesis, and is capable of synthesizing proteins without killing the organism. In addition, because the production of protein does not accompany operations of culture and the like, the protein can be synthesized in a short time as compared to cell-systems. Moreover, inasmuch as the cell-free protein synthesis also affords a large scale production of proteins consisting of amino acid sequences not utilized by the organism, it is expected to be a promising expression method. As a cell rupture or extract solution to be applied to the cell-free protein synthesis, use of various substances of biological derivation has been considered and investigations are underway. Of these, since yeast can be easily cultured like prokaryotes such as *Escherichia coli* and the like, its extract solution can be obtained at a low cost. Since yeast is an eukaryote, posttranslational modification such as glycosylation and the like, which is not applicable to extract solutions of *Escherichia coli* and the like, can be applied. In view of the above, the development of yeast-derived extract solutions for cell-free protein synthesis has been drawing much attention.

A cell-free protein synthesis method using a yeast-derived extract solution was first reported by Gasior et al. (for example, Gasior, E. et al., J. Biol. Chem., 254, 3965-3969, 1979). According to the method of Gasior et al., yeast is first cultured, spheroplast is prepared using glusulase and then cultured again in YM-5 medium containing 0.4 M $MgSO_4$. Then cells are recovered again by centrifugation, suspended in a buffer and ruptured with a Dounce homogenizer. The rupture is subjected to centrifugation at 30,000xg, then at 100,000xg. The obtained supernatant is applied to Sephadex G-25 and the fractions having a high protein content are collected to give an extract solution for cell-free protein synthesis. However, the method of Gasior et al. requires very complicated preparation of an extract solution, requiring considerable time and labor therefor.

To solve this problem, Hussain et al. developed a more convenient preparation method of a extract solution for cell-free protein synthesis, by changing the method of cell rupture (for example, Hussain, I et al., Gene, 46, 13-23, 1986). The method proposed by Hussain et al., which is a highly convenient production method of an extract solution, comprises culturing yeast, collecting cells, washing the cells with a buffer, suspending and then rupturing the cells with glass beads, centrifuging the obtained rupture at 30,000xg and subjecting the obtained supernatant to Sephadex G-25.

In addition, US2002/0168705 A1 (JP-A-2002-262867) discloses a cell-free synthesis method of a heavy atom isomorphous replacement product protein, which is suitable for X-ray crystallographic analysis of a protein using an extract solution derived from yeast and the like.

However, the amount of protein synthesized using the extract solution obtained by any of the above-mentioned methods is extremely small, and the protein synthesis activity can be measured only by the uptake of the radiation-labeled amino acid. Therefore, a method for preparing a yeast-derived extract solution, which is easily prepared and capable of synthesizing a high amount of protein, has been desired.

SUMMARY OF THE INVENTION

The present invention has been made to solve the above-mentioned problems and aims at providing a preparation method of a yeast extract solution for cell-free protein synthesis, which solution is easy to prepare and is capable of synthesizing a higher amount of a protein than by conventional yeast extract solutions, the yeast extract solution, a cell-free protein synthesis method using the yeast extract solution, and a kit for cell-free protein synthesis, which contains the yeast extract solution.

As a result of the intensive studies conducted by the present inventors in an attempt to solve the above-mentioned problems, the present invention has been completed. Accordingly, the present invention provides the following.

(1) A method for preparing a yeast extract solution for cell-free protein synthesis, which comprises rupturing a yeast cell in a frozen state and obtaining an extract solution thereof.

(2) The preparation method of the above-mentioned (1), wherein the yeast cell is frozen with liquid nitrogen.

(3) The preparation method of the above-mentioned (1) or (2), wherein the yeast cell is mashed in a mortar with a pestle.

(4) The preparation method of any of the above-mentioned (1) to (3), further comprising, after the extraction from a yeast cell, removing intracellular components having a molecular weight of not more than 5,000 from the extract solution and concentrating the resulting solution.
(5) A yeast extract solution for cell-free protein synthesis, which is prepared by the method of any of the above-mentioned (1) to (4).
(6) A cell-free synthesis method of a protein, which comprises using a reaction solution containing the yeast extract-solution of the above-mentioned (5).
(7) The method of the above-mentioned (6), wherein the reaction solution is adjusted to pH 6.0-8.0.
(8) The method of the above-mentioned (6), which comprises dialyzing the reaction solution while synthesizing a protein.
(9) A kit for cell-free protein synthesis, which comprises the yeast extract solution of the above-mentioned (5).

DETAILED DESCRIPTION OF THE INVENTION

Figure 1:
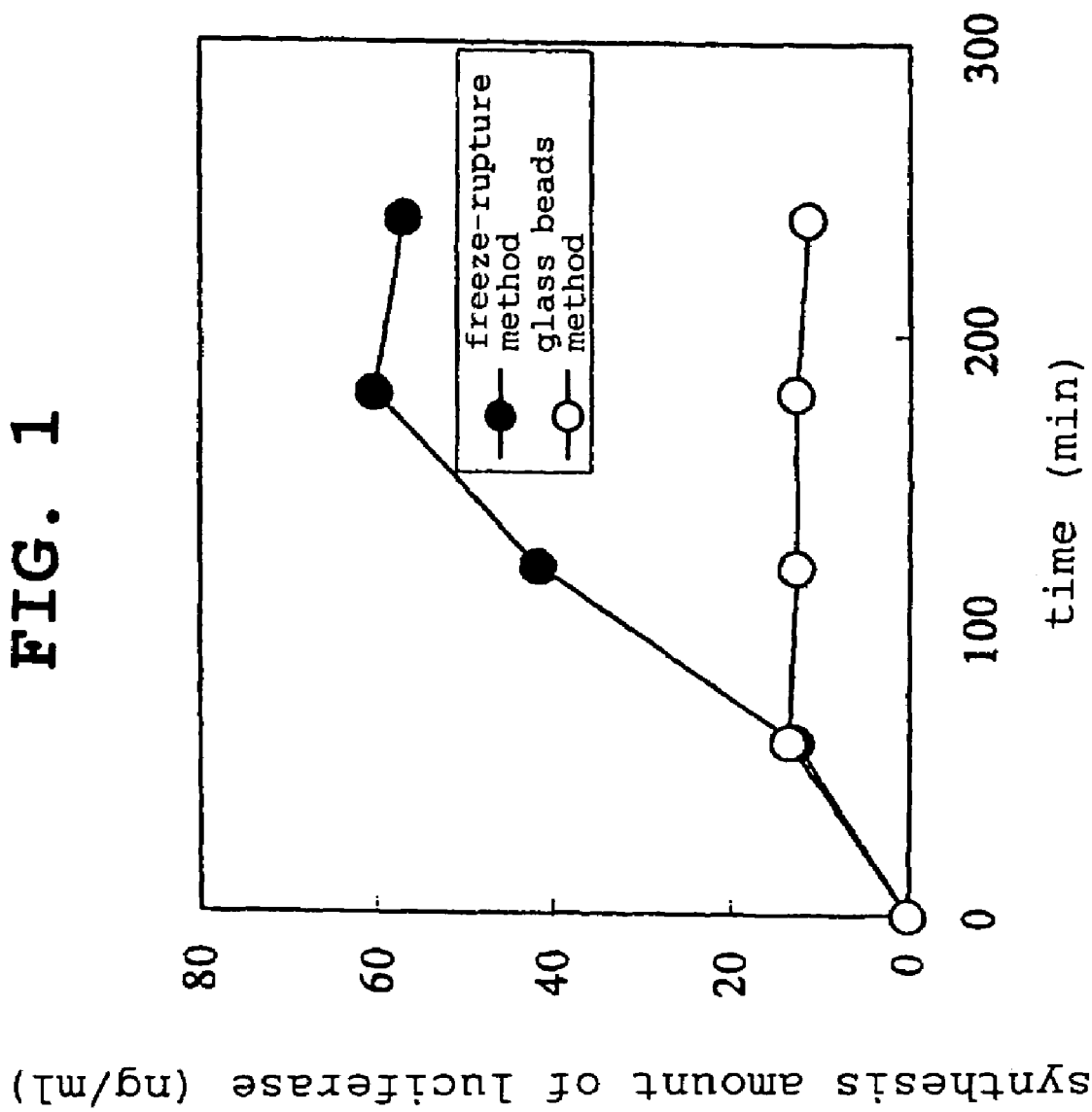
FIG. 1 is a graph showing an amount of synthesized luciferase in each reaction time using the yeast extract solutions of Example 1 and Comparative Example 1, wherein the axis of ordinate shows the amount of synthesized luciferase (ng/mL) and the axis of abscissa shows the reaction time (min).

The "cell-free protein synthesis" in the present specification means a protein synthesis using a cell-free translation system to synthesize a protein by reading the information of mRNA. As used herein, the "protein" synthesized in the cell-free system according to the synthesis method of the present invention encompasses any peptide having any molecular weight, which consists of plural amino acid residues, i.e., from low molecular weight peptides to high molecular weight peptides. The "protein" in the present specification includes glycosylated glycoproteins.

EMBODIMENT OF THE INVENTION

The present invention is explained in detail in the following.

The present invention relates to a method for preparing a yeast extract solution for cell-free protein synthesis, which comprises rupturing a frozen yeast cell and obtaining an extract solution from the yeast cell. By preparing a yeast extract solution by such method, the cells can be ruptured more conveniently than by the method described in Gasior, E. et. al., J. Biol. Chem., 254, 3965-3969, 1979 and under milder conditions than by the method described in Hussain, I et. al., Gene, 46, 13-23, 1986.

The preparation method of the present invention requires freezing a yeast cell. The yeast cell is desirably frozen rapidly using an inert gas such as liquid nitrogen and the like. When the cell is not rapidly frozen, the components necessary for protein synthesis may be inconveniently inactivated and the like, and the above-mentioned effect of the present invention may not be achieved certainly.

The above-mentioned freezing of the yeast cell can be realized by, for example, using the above-mentioned liquid nitrogen, aceton-dry ice and the like. It is preferable to use liquid nitrogen because the use of an organic solvent such as aceton and the like may inactivate components necessary for the protein synthesis.

As mentioned above, the yeast cell is frozen and ruptured in a freezing state. The yeast cell may be ruptured by any method as long as the frozen yeast cell is powdered. For example, the cell may be mashed in a mortar with a pestle, may be pulverized using a metal corn as a pulverizing medium and a multi-beads shocker (produced by YASUI KIKAI CORPORATION) or other method. The yeast cell is preferably ruptured by mashing in a mortar with a pestle, because the yeast cell can be ruptured under milder conditions, and substances unnecessary for cell-free protein synthesis are not extracted from the yeast cell.

As the "yeast" in the present invention, any of the sporogenous yeast, basidiomycetous yeast and asporogenous yeast can be used without any particular limitation as long as it is conventionally recognized generally as a yeast. Of these, sporogenous yeast is preferably used. Of the sporogenous yeasts, fission yeast is more preferably used, and of the fission yeasts, *Schizosaccaromyces pombe* is particularly preferably used.

Extraction in the present invention may be performed from a single species of yeast cell or from plural species of yeast cells.

According to the method of the present invention, extraction from a ruptured yeast cell is conducted by adding a solution for extraction to a yeast cell after the above-mentioned rupture. The solution for extraction to be used is not particularly limited, but it preferably contains at least a protease inhibitor. When a solution for extraction containing a protease inhibitor is used, the activity of protease contained in the yeast-derived extract is inhibited and undesired degradation of active protein in the extract due to the protease can be prevented. As a result, the protein synthesis ability possessed by the yeast-derived extract can be effectively drawn.

The above-mentioned protease inhibitor is not particularly limited as long as it can inhibit the activity of protease, and, for example, phenylemethanesulfonyl fluoride (hereinafter sometimes to be referred to as "PMSF"), aprotinin, bestatin, leupeptin, pepstatin A, E-64 (L-trans-epoxysuccinyl-L-leucylamido (4-guanidino)butane), ethylenediaminetetraacetic acid, phosphoramidon and the like can be used. Since the inside of the yeast cell is assumed to have a strong serine protease activity, the use of PMSF, which acts as an inhibitor having high specificity to serine protease, is preferable among those mentioned above. Moreover, it is possible to use not only one kind of a protease inhibitor but also a mixture (protease inhibitor cocktail) of several kinds of protease inhibitors.

The content of the protease inhibitor in the solution for extraction is free of any particular limitation, but it is preferably 1 µM-50 mM, more preferably 0.01 mM-5 mM, because decomposition of the enzyme necessary for the action of the present invention can be preferably inhibited. This is because the decomposition activity of protease often cannot be suppressed sufficiently when the protease inhibitor is less than 1 µM, and the protein synthesis reaction tends to be inhibited when the protease inhibitor exceeds 50 mM.

The solution for extraction of the present invention preferably contains, in addition to the above-mentioned protease inhibitor, at least a potassium salt, a magnesium salt, dithiothreitol and a buffer.

The above-mentioned potassium salt is free of any particular limitation as long as it does not inhibit the action of the present invention, and can be used in a general form, such as potassium acetate, potassium carbonate, potassium hydrogen carbonate, potassium chloride, dipotassium hydrogenphosphate, dipotassium hydrogen citrate, potassium sulfate, potassium dihydrogenphosphate, potassium iodide, potassium phthalate and the like, with preference given to potassium acetate. Potassium salt acts as a cofactor in the protein synthesis reaction.

The content of potassium salt in the solution for extraction is free of any particular limitation, but from the aspect of preservation stability, it is preferably 1 mM-500 mM, more preferably 10 mM-300 mM, in the case of a monovalent potassium salt, such as potassium acetate and the like. When the content of the potassium salt is less than 1 mM or more than 500 mM, the components essential for protein synthesis tend to become unstable.

The above-mentioned magnesium salt is free of any particular limitation as long as it does not inhibit the action of the present invention, and can be used in a general form such as magnesium acetate, magnesium sulfate, magnesium chloride, magnesium citrate, magnesium hydrogen phosphate, magnesium iodide, magnesium lactate, magnesium nitrate, magnesium oxalate and the like, with preference given to magnesium acetate. Magnesium salt also acts as a cofactor in the protein synthesis reaction.

The content of the magnesium salt in the solution for extraction is free of any particular limitation, but from the aspect of preservation stability, it is preferably 0.01 mM-10 mM, more preferably 0.1 mM-5 mM, in the case of a divalent salt, such as magnesium acetate and the like. When the content of magnesium salt is less than 0.01 mM or more than 10 mM, the components essential for protein synthesis tend to become unstable.

The above-mentioned dithiothreitol (hereinafter sometimes to be referred to as "DTT") is added for prevention of oxidization, and is preferably contained in an amount of 0.01 mM-10 mM, more preferably 0.1 mM-5 mM, in the solution for extraction. When the content of DTT is less than 0.01 mM or more than 10 mM, the components essential for protein synthesis tend to become unstable.

The above-mentioned buffer imparts a buffer capacity to a solution for extraction, and is added for prevention of denaturation of an extract caused by radical change in pH of the solution for extraction due to, for example, the addition of an acidic or basic substance and the like. Such buffer is free of any particular limitation, and, for example, HEPES-KOH, Tris-HCl, acetic acid-sodium acetate, citric acid-sodium citrate, phosphoric acid, boric acid, MES, PIPES and the like can be used.

The buffer is preferably one that maintains the pH of the solution for extraction at 4-10, more preferably 6-8. When the pH of the solution for extraction is less than 4 or more than 10, the components essential for the reaction of the present invention may be denatured. From this aspect, the use of HEPES-KOH (pH 6-8) is particularly preferable among the above-mentioned buffers.

While the content of the buffer in the extract solution is free of any particular limitation, it is preferably 5 mM-200 mM, more preferably 10 mM-100 mM, to maintain preferable buffer capacity. When the content of the buffer is less than 5 mM, the pH tends to change radically due to the addition of an acidic or basic substance, which in turn may cause denaturation of the extract, and when the content of the buffer exceeds 200 mM, the salt concentration becomes too high and the components essential for protein synthesis tend to become unstable.

In the preparation method of the yeast extract of the present invention, the steps from the extraction from the yeast cell after the above-mentioned rupture, to the obtainment of the yeast extract solution for cell-free protein synthesis are not particularly limited and, for example, the following procedure may be employed.

First, a solution for extraction is added to the yeast cell after the above-mentioned rupture and the obtained liquid containing the yeast extract is applied to centrifugation. The centrifugation is performed under the conditions generally employed in this field (10,000xg-50,000xg, 0° C.-10° C., 10 min-60 min). The supernatant is recovered and again subjected to centrifugation under the above-mentioned conditions.

After the centrifugation, the supernatant is applied to gel filtration. As the gel filtration, for example, desalting column PD-10 (manufactured by Amersham Biosciences) can be preferably used. According to a conventional method, the column is equilibrated with a solution for extraction containing 20% glycerol a sample is fed, and the mixture is eluted with the above-mentioned solution for extraction. These conditions can be also employed in the present invention. The above-mentioned buffer solution for gel filtration is preferably a solution for extraction supplemented with glycerol. Using this, the components essential for protein synthesis are beneficially stabilized. Glycerol only need to be added at generally 5 (v/v) %-40 (v/v) %.

The filtrate obtained by gel filtration may be fractionated into 0.1 mL-1 mL fractions as in general gel filtration, and 0.4 mL-0.6 mL is preferably used as one fraction for efficiently obtaining a fraction having high protein synthesis ability.

Subsequently, a fraction having an absorbance at 280 nm of not less than 20 and an absorbance at 260 nm of not less than 30 is separated from the filtrate after gel filtration, using instruments such as Ultrospec 3300 pro (manufactured by Amersham Biosciences), to give the yeast extract solution of the present invention.

The yeast cell to be subjected to the preparation method of the present invention is preferably washed prior to the above-mentioned rapid freezing with the aforementioned solution for extraction having a preferable composition, so that inhibition of the protein synthesis reaction due to medium components and the like can be prevented. For washing with a solution for extraction, a solution for extraction is added to a yeast cell, and the mixture is subjected to centrifugation (e.g., 4° C., 8,000xg, 5 min).

The amount of the solution for extraction to be used for washing is preferably 1 mL-20 mL, more preferably 2 mL-15 mL, per 1 g of (wet weight) of the yeast cell, to completely remove the medium.

The amount of the yeast cell to be subjected to the preparation method of the present invention is not particularly limited.

The extract solution for cell-free protein synthesis prepared by the method of the present invention preferably contains a yeast-derived extract in a proportion of 1 mg/mL-200 mg/mL, more preferably 10 mg/mL-100 mg/mL. When the content of the extract derived from yeast is less than 1 mg/mL, the concentration of the components essential for the protein synthesis becomes low and a sufficient amount may not be synthesized. When the content of the extract derived from a yeast exceeds 200 mg/mL, synthesis reaction time may be markedly shortened because it contains many extracted factors that inhibit protein synthesis reaction.

The protein content of the extract derived from yeast in the extract solution can be measured, for example, using BCA Protein Assay Kit (manufactured by PIERCE). The steps therefor include adding 0.1 mL of a sample to a reaction reagent (2 mL), reacting the mixture at 37° C. for 30 min, and measuring the absorbance at 562 nm. As a control, bovine serum albumin is generally used.

Whether the extract contained in the extract solution is derived from a yeast can be determined by, for example, analyzing the base sequence of ribosomal RNA contained in the extract.

The extract solution of the present invention is preferably realized to contain the extract derived from yeast in a proportion of 1 mg/mL-200 mg/mL in a protein concentration, together with 1 mM-500 mM of potassium acetate, 0.01 mM-10 mM of magnesium acetate, 0.01 mM-10 mM of DTT, 1 μM-50 mM of PMSF and 5 mM-200 mM of HEPES-KOH (pH 6-8).

In addition, the extract solution of the present invention is preferably subjected, after being obtained by the above-mentioned preparation method, to removal of intracellular components having a molecular weight of 5,000 or below (preferably 10,000 or below), and concentrated. By the concentration, the components unnecessary for the protein synthesis can be removed, and concentration of the necessary components increases the reaction speed of the protein synthesis.

The method of the above-mentioned concentration is not particularly limited and a conventionally known appropriate method can be employed. The concentration is performed in such a manner that the absorbance at 280 nm of an extract solution after the concentration preferably becomes 10-100, more preferably 20-80. When the above-mentioned absorbance of the extract solution after concentration is less than 10, the protein synthesis rate becomes slow and, as a result, synthesis amount tends to not increase. When the above-mentioned absorbance exceeds 100, the synthesis rate increases but synthesis amount tends to not increase because the synthesis reaction time is extremely shortened.

The method for concentrating the extract solution is not particularly limited, and conventionally known various methods, such as ultrafree-0.5 centrifugal filter & tube (exclusion molecular weight: 10,000 or below, manufactured by Millipore) and the like, can be used.

The present invention also provides a method for cell-free protein synthesis using the above-mentioned extract solution. In the synthesis reaction, the reaction solution to be generally prepared contains the above-mentioned extract solution and an additive necessary for cell-free protein synthesis. The above-mentioned additive is not particularly limited and any additive can be used as long as it is conventionally used in the field of cell-free protein synthesis.

The above-mentioned reaction solution is preferably prepared in such a manner that the extract solution of the present invention is contained in a proportion of 10 (v/v) %-90 (v/v) %, particularly 20 (v/v) %-80 (v/v) %.

That is, the content of the extract derived from yeast cells in the above-mentioned reaction solution as a whole is preferably prepared to be 0.1 mg/mL-180 mg/mL, more preferably 2 mg/mL-80 mg/mL. When the content of the extract is less than 0.1 mg/mL or above 180 mg/mL in a protein concentration, the synthesis rate of the object protein tends to become unpreferably low.

The reaction solution to be used for the method for cell-free protein synthesis of the present invention is preferably adjusted to pH 6.0-8.0, more preferably 6.5-7.5 (conventional general reaction solution for cell-free protein synthesis has pH of 7.4-7.6). When the pH of the reaction solution is lower than 6.0, the components essential for the protein synthesis may be denatured, and a pH exceeding 8.0 is not preferable for the components essential for protein synthesis, because the reaction rate tends to become low.

Generally, the above-mentioned reaction solution contains, as components other than the above-mentioned extract solution, at least potassium salt, magnesium salt, DTT, adenosine 5'-triphosphate, guanosine 5'-triphosphate, creatine phosphate, creatine kinase, amino acid component, RNase inhibitor, tRNA, mRNA and buffer. This advantageously realizes a reaction solution for cell-free protein synthesis, which is further capable of synthesizing a large amount of protein in a short time.

As the potassium salt in the reaction solution, various potassium salts described above as a component of solution for extraction, preferably potassium acetate, can be preferably used. The potassium salt is preferably contained in the reaction solution in a proportion of 10 mM-500 mM, more preferably 20 mM-300 mM, from the same aspect of the potassium salt in the aforementioned solution for extraction.

As a magnesium salt in the reaction solution, various magnesium salts described above as a component of solution for extraction, preferably magnesium acetate, can be preferably used. The magnesium salt is preferably contained in the reaction solution in a proportion of 0.1 mM-10 mM, more preferably 0.5 mM-5 mM, from the same aspect of the magnesium salt in the aforementioned extract solution.

DTT is preferably contained in the reaction solution in a proportion of 0.01 mM-10 mM, more preferably 0.1 mM-5 mM, from the same aspect of DTT in the aforementioned solution for extraction.

The adenosine 5'-triphosphate (hereinafter sometimes to be referred to as "ATP") is preferably contained in the reaction solution in a proportion of 0.01 mM-2 mM, more preferably 0.1 mM-1 mM, in view of the rate of protein synthesis. When ATP is contained in a proportion of less than 0.01 mM or above 2 mM, the synthesis rate of the protein tends to become lower.

The guanosine 5'-triphosphate hereinafter sometimes to be referred to as "GTP") in the reaction solution preferably contained in the reaction solution in a proportion of 0.01 mM-10 mM, more preferably 0.2 mM-5 mM, in view of the rate of protein synthesis. When GTP is contained in a proportion of less than 0.01 mM or above 5 mM, the synthesis rate of the protein tends to become lower.

The creatine phosphate in the reaction solution is a component for continuous synthesis of protein and added for regeneration of ATP and GTP. The creatine phosphate is preferably contained in the reaction solution in a proportion of 10 mM-50 mM, more preferably 15 mM-35 mM, in view of the rate of protein synthesis. When creatine phosphate is contained in a proportion of less than 10 mM, sufficient amounts of ATP and GTP may not be regenerated easily. As a result, the rate of protein synthesis tends to become lower. When the creatine phosphate content exceeds 50 mM, it acts as an inhibitory substance and the rate of protein synthesis tends to become lower.

The creatine kinase in the reaction solution is a component for continuous synthesis of protein and added along with creatine phosphate for regeneration of ATP and GTP. The creatine kinase is preferably contained in the reaction solution in a proportion of 1 μg/mL-1000 μg/mL, more preferably 10 μg/mL-500 μg/mL, in view of the rate of protein synthesis. When the creatine kinase content is less than 1 μg/mL, sufficient amount of ATP and GTP may not be regenerated. As a result, the rate of protein synthesis tends to become lower. When the creatine kinase content exceeds 1000 μg/mL, it acts as an inhibitory substance and the synthesis rate of the protein tends to become lower.

The amino acid component in the reaction solution contains at least 20 kinds of amino acids, i.e., valine, methionine, glutamic acid, alanine, leucine, phenylalanine, glycine, proline, isoleucine, tryptophan, asparagine, serine, threonine, histidine, aspartic acid, tyrosine, lysine, glutamine, cysteine and arginine. The amino acid component generally contains almost an equivalent amount each of the above-mentioned 20 kinds of amino acids.

In the present invention, the above-mentioned amino acid component is preferably contained in the reaction solution in a proportion of 1 μM-1000 μM, more preferably 10 μM-500 μM, in view of the rate of protein synthesis. When the amount of the amino acid component is less than 1 μM or above 1000 μM, the synthesis rate of the protein tends to become lower.

The RNase inhibitor in the reaction solution is added to prevent RNase, which is derived from yeast cells contaminating extract solution, from undesirably digesting mRNA and tRNA, thereby preventing synthesis of protein, during cell-free protein synthesis of the present invention. It is preferably contained in the reaction solution in a proportion of 0.1 U/μL-20 U/μL, more preferably 0.2 U/μL-10 U/μL. When the amount of RNase inhibitor is less than 0.1 U/μL, the degradation activity of RNase often cannot be suppressed sufficiently, and when the amount of the RNase inhibitor exceeds 20 U/μL, protein synthesis reaction tends to be inhibited.

As regards exogenous mRNA in the reaction solution, a protein (including peptide) to be encoded thereby is not particularly limited, and the mRNA may encode a toxic protein or a glycoprotein. The mRNA to be used is not particularly limited as regards the number of bases and all the mRNAs may not have the same number of bases as long as they can synthesize the object protein. In addition, as long as the sequences are homologous to the extent that the object protein can be synthesized, plural bases of each mRNA may be deleted, substituted, inserted or added.

The mRNA to be used in the present invention may be an appropriate commercially available one. When an mRNA obtained by transcription reaction using a vector derived from $pT_NT$ vector (manufactured by Promega), wherein start codon of DNA encoding the object protein is inserted into the downstream of 5'-β globin leader sequence, is used, the efficiency of the cell-free transcription reaction is improved, which in turn preferably affords a large amount of an object protein.

In the reaction solution, mRNA is preferably contained in a proportion of 1 μg/mL-1000 μg/mL, more preferably 10 μg/mL-500 μg/mL, in view of the rate of the protein synthesis. When mRNA is less than 1 μg/mL or more than 1000 μg/mL, the rate of the protein synthesis tends to decrease.

The tRNA in the reaction solution contains almost the same amount of each of the tRNAs corresponding to the above-mentioned 20 kinds of amino acids. In the present invention, tRNA is preferably contained in the reaction solution in a proportion of 1 μg/mL-1000 μg/mL, more preferably 10 μg/mL-500 μg/mL, in view of the rate of protein synthesis. When the amount of tRNA is less than 1 μg/mL or exceeds 1000 μg/mL, the rate of protein synthesis tends to become lower.

The buffer to be contained in the reaction solution is preferably similar to the buffers used for the aforementioned extract solution of the present invention, and the use of HEPES-KOH (pH 6-8) is preferable for the same reasons. The buffer is preferably contained in an amount of 5 mM-200 mM, more preferably 10 mM-100 mM, from the same aspect of the aforementioned buffer contained in the extract solution.

The above-mentioned reaction solution more preferably contains a glycerol. When glycerol is added, the components essential for the protein synthesis can be advantageously stabilized in the protein synthesis reaction. When glycerol is added, the amount is generally to be 5 (v/v) %-20 (v/v) %.

That is, the reaction solution to be used for the cell-free protein synthesis method of the present invention is preferably realized to contain, besides 10 (v/v) %-90 (v/v) % of the above-mentioned extract solution, 10 mM-500 mM of potassium acetate, 0.1 mM-10 mM of magnesium acetate, 0.01 mM-10 mM of DTT, 5 (v/v) %-20 (v/v) % of glycerol, 0.01 mM-2 mM of ATP, 0.01 mM-10 mM of GTP, 10 mM-50 mM of creatine phosphate, 1 μg/mL-1000 μg/mL of creatine kinase, 1 μM-1000 μM of amino acid component, 0.1 U/μL-20 U/μL of RNase inhibitor, 1 μg/mL-1000 μg/mL of tRNA, 1 μg/mL-1000 μg/mL of mRNA and 5 mM-200 mM of HEPES-KOH (pH 6-8).

The cell-free protein synthesis method of the present invention is performed using the extract solution of the present invention as mentioned above in, for example, a conventionally known low temperature incubator. For reaction, the reaction solution containing the above-mentioned extract solution is generally prepared and used.

The reaction temperature is generally within the range of 10° C.-40° C., preferably 15° C.-35° C. When the reaction temperature is lower than 10° C., the synthesis rate of the protein tends to become lower, and when the reaction temperature exceeds 40° C., the essential components tend to be denatured.

In the cell-free protein synthesis method of the present invention, moreover, a protein is preferably synthesized while dialyzing a yeast extract solution. By synthesizing a protein while performing dialysis in this way, an energy source necessary for protein synthesis of ATP and the like is constantly supplied from an outer solution for dialysis, thereby advantageously extending the protein synthesis reaction time.

When a protein is synthesized while dialyzing a yeast extract solution, a reaction solution contained in a dialysis membrane is filled in a reaction bath containing an outer solution for dialysis, thereby to carry out a protein synthesis reaction.

The dialysis membrane to be used is not particularly limited, and conventionally known various membranes may be used. A membrane capable of dispersing a substance having a molecular weight of 3,000 or below, particularly 10,000 or below, from a reaction solution into an outer solution for dialysis is preferable. As such dialysis membrane, for example, Slide-A-Lyzer (manufactured by PIERCE, exclusion molecular weight: 10,000 or below) and the like can be mentioned.

The outer solution for dialysis to be used is not particularly limited as long as it has a composition permitting the above-mentioned dialysis. For example, an outer solution for dialysis reaction solution having a composition excluding the extract solution, tRNA, mRNA, creatine kinase and RNase inhibitor from the composition of the reaction solution can be used.

The present invention relates to a kit for cell-free protein synthesis, which contains a yeast extract solution of the present invention. The yeast extract solution to be contained in the kit is preferably free of intracellular components having a molecular weight of 5000 or below, and after concentration. Preferably, the kit further contains a part or all of a potassium salt, a magnesium salt, DTT, adenosine 5'-triphosphate, guanosine 5'-triphosphate, creatine phosphate, creatine kinase, an amino acid component, an RNase inhibitor, tRNA and a buffer. These components are contained in the kit in the form of a powder or a solution. These components may be contained in the kit in the form of a partially or entirely mixed powder or a solution. More preferably, the kit contains the aforementioned dialysis membrane and/or a dialysis outer solution. The constituent components of the kit are preferably separately packaged and contained in a single package.

The amount of the protein synthesized by the cell-free protein synthesis method of the present invention can be determined by measurement of enzyme activity, SDS-PAGE, immunoassay and the like.

The protein that can be synthesized by the cell-free protein synthesis method of the present invention is free of any particular limitation.

EXAMPLES

The present invention is explained in more detail in the following by referring to Examples. The following examples do not limit the present invitation.

Reference Example 1

Culture of Yeast (*Schizosaccaromyces pombe*) Cell

*Schizosaccaromyces pombe* was inoculated to a large-mouth test tube containing 6 mL of YEPD medium (glucose: 1.0%, yeast extract: 1.0%, polypepton: 2.0%) and cultured with shaking at 30° C. for 16 hr. Using this as a pre-culture medium, 10 mL thereof was inoculated to a YEPD medium (2.5 L) containing 0.5 μM of thiamine and cultured under aeration with stirring at 30° C. for about 15 hr until absorbance at 660 nm became 1.0. The culture medium was subjected to centrifugation (4° C., 8,000xg, 5 min) and the cells were harvested. As a result, about 6 g of wet cells were obtained from 2.5 L of a culture medium.

Example 1

Preparation of Yeast Extract Solution for Cell-Free Protein Synthesis

The yeast cells obtained in the above-mentioned Reference Example 1 were washed with distilled water, and the cells were harvested again by centrifugation (4° C., 8,000xg, 5 min). The cells were washed with 3 mL of a solution for extraction having the following composition per 1 g (wet weight) of the cells.

[Composition of Solution for Extraction]
50 mM HEPES-KOH (pH 7.0)
100 mM potassium acetate
2 mM magnesium acetate
2 mM DTT The cells were again recovered by centrifugation (4° C., 8,000xg, 5 min). The recovered cells (ca. 5 g) were placed in a mortar frozen at −80° C. Thereto was added liquid nitrogen, and the mixture was vigorously mashed in the mortar using a pestle. To the mashed cells was added a solution for extraction (4.5 mL) containing 0.5 mM PMSF, and the mixture was extracted. After the extraction, the residue of the cells was removed by centrifugation (4° C., 30,000xg, 10 min), and the obtained supernatant was subjected to centrifugation (4° C., 30,000xg, 30 min) again. The supernatant (2.0 mL) after the centrifugation was applied to PD-10 (manufactured by Amersham Biosciences), which was equilibrated with a solution for extraction containing 20 (v/v) % glycerol, and eluted with the same solution for extraction. The eluate was fractionated by 500 μL. The absorbance of each fraction at 280 nm and 260 nm was measured and fractions having absorbance of not less than 20 and 30, respectively, were collected to give an extract solution derived from yeast for cell-free protein synthesis. By this operation, about 1.5 mL of an extract solution having an absorbance at 280 nm and 260 nm of 25 and 42, respectively, was obtained.

Comparative Example 1

Production of Yeast Extract Solution by Glass Bead Method

The yeast cells obtained in the above-mentioned Reference Example 1 were washed with distilled water and subjected to centrifugation (4° C., 8,000xg, 5 min) to recover cells again. The cells were washed with 3 mL of a solution for extraction having the following composition per 1 g (wet weight) of the cells.

[Composition of Solution for Extraction]
50 mM HEPES-KOH (pH 7.0)
100 mM potassium acetate
2 mM magnesium acetate
2 mM DTT The cells were again recovered by centrifugation (4° C., 8,000xg, 5 min). The recovered cells (ca. 5 g) were suspended in a solution for extraction (5 mL) containing 0.5 mM PMSF and glass beads (10 g) were added. The yeast cells were ruptured using a Multi-beads shocker (produced by YASUI KIKAI CORPORATION) at 2,500 rpm for 30 sec, 10 cycles. After rupture, the residual cells were removed by centrifugation (4° C., 8,000xg, 5 min). The obtained supernatant was subjected to centrifugation (4° C., 30,000xg, 10 min) and the obtained supernatant was subjected to centrifugation (4° C., 30,000xg, 30 min) again. The obtained supernatant (2.0 mL) was applied to PD-10 (manufactured by Amersham Biosciences), which was equilibrated with a solution for extraction containing 20 (v/v) % glycerol, and eluted with the same solution for extraction. The eluate was fractionated by 500 μL. The absorbance of each fraction at 280 nm and 260 nm was measured and fractions having absorbance of not less than 90 and 150, respectively, were collected to give an extract solution derived from yeast for cell-free protein synthesis. By this operation, about 1.5 mL of an extract solution having an absorbance at 280 nm and 260 nm of 110 and 180, respectively, was obtained.

Experimental Example 1

Cell-Free Protein Synthesis Using Extract Solutions Obtained in Example 1 and Comparative Example 1

Using the extract solutions obtained in the above-mentioned Example 1 and Comparative Example 1, a reaction solution having the following composition was prepared.

[Composition of Reaction Solution]
  50 (v/v) % yeast extract solution
  25 mM HEPES-KOH (pH 7.0)
  50 mM potassium acetate
  2 mM magnesium acetate
  1 mM DTT
  10 (v/v) % glycerol
  0.5 mM ATP
  0.1 mM GTP
  25 mM creatine phosphate
  200 µg/mL creatine kinase
  40 µM amino acid (20 kinds)
  1 U/µL RNase inhibitor (derived from human placenta)
  200 µg/mL tRNA (derived from yeast)
  20 µg/mL mRNA As the mRNA, mRNA (luciferase control RNA, manufactured by Promega) encoding luciferase was used. Using low temperature dyr block G-1000 (manufactured by TOKYO RIKAKIKAI Co.) as a reaction apparatus, a synthesis reaction of protein was performed in a cell-free system. The reaction temperature was 30° C. and the amount of the reaction solution was 25 µL. The synthesized luciferase was quantified using a luciferase assay kit (E-1500, manufactured by Promega). A reaction solution (2.5 µL) was added to a luciferase assay reagent (50 µL) and luminescence by luciferase was measured using a luminometer (Turner Designs TD-20/20, manufactured by Promega).

FIG. 1 is a graph showing the amount of synthesized luciferase in each reaction time using the yeast extract solutions of Example 1 and Comparative Example 1. In FIG. 1, the axis of ordinate shows the amount of synthesized luciferase (ng/mL) and the axis of abscissa shows the reaction time (min). As shown in FIG. 1, the protein synthesis reaction using the yeast extract solution prepared by freeze-rupture method lasted for 3 hr after the start of the reaction, and 60 ng/mL of luciferase was synthesized. In contrast, the synthesis reaction using the yeast extract solution prepared by a glass bead method stopped in 1 hr and the amount of synthesized luciferase was 14 ng/mL.

Experimental Example 2

Cell-Free Protein Synthesis Using Concentrated Extract Solution

The extract solution prepared in the above-mentioned Example 1 was concentrated serially by an ultrafree-0.5 centrifugal filter & tube (manufactured by Millipore, exclusion molecular weight: 10,000 or below) to give concentrated extract solutions having an absorbance at 280 nm of 22, 37, 50, 62 and 74. Using respective concentrated extract solutions, reaction solutions having the same composition as in the above-mentioned Experimental Example 1 were prepared and subjected to cell-free protein synthesis. The synthesized luciferase was quantified in the same manner as in Experimental Example 1.

Figure 2:
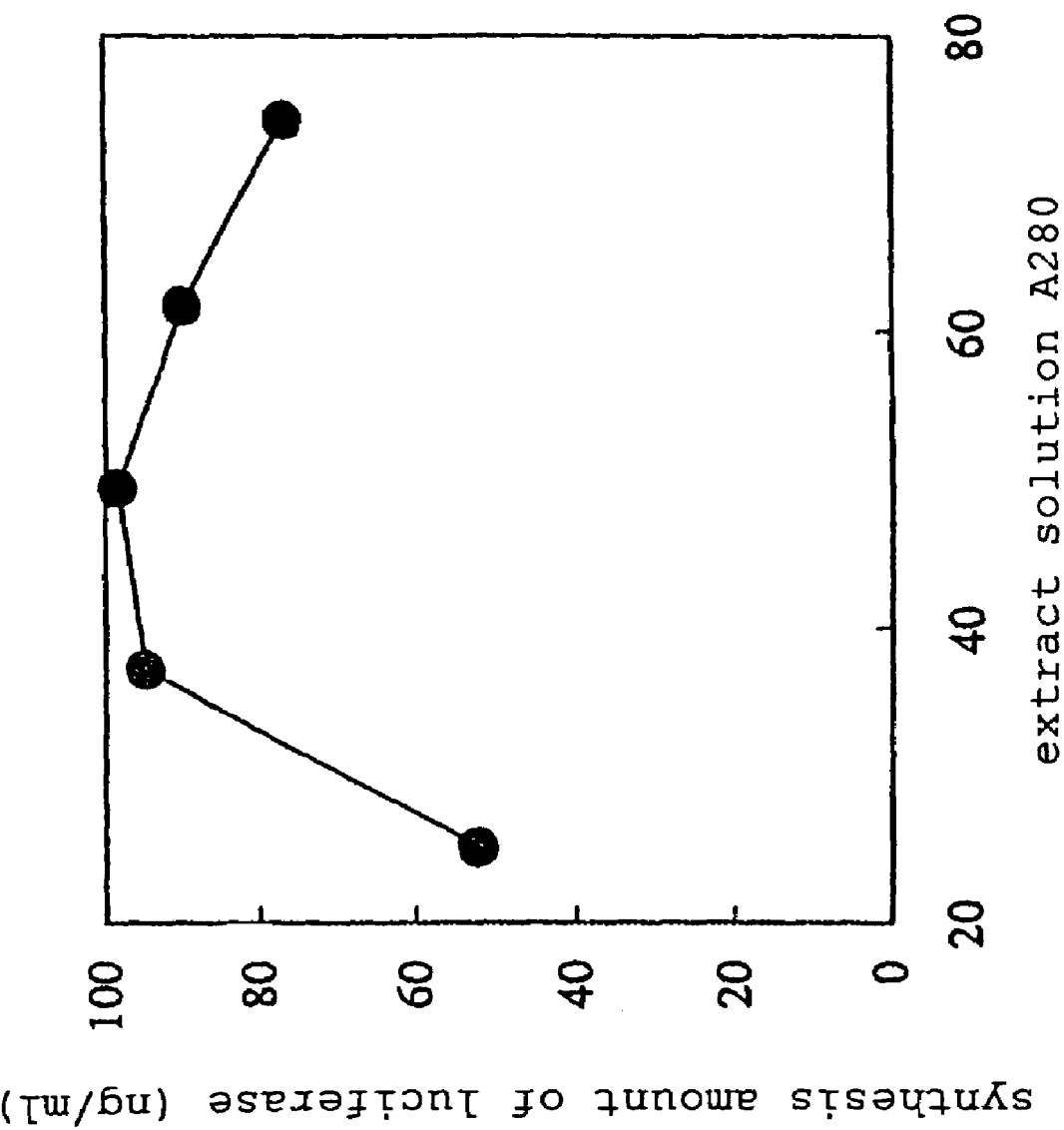
FIG. 2 is a graph showing an amount of synthesized luciferase in 3 hr from the start of the synthesis reaction using the concentrated extract solution, wherein the axis of ordinate shows the amount of synthesized luciferase (ng/mL) and the axis of abscissa shows the absorbance at 280 nm of the extract solution.

FIG. 2 is a graph showing the amount of synthesized luciferase in 3 hr from the start of the synthesis reaction using the concentrated extract solution. In FIG. 2, the axis of ordinate shows the amount of synthesized luciferase (ng/mL) and the axis of abscissa shows the absorbance at 280 nm of the extract solution. As shown in FIG. 2, the concentrated extract solution having an absorbance at 280 nm of the extract solution of 35-50 showed the highest synthesis amount, synthesizing about 100 ng/mL of luciferase.

Reference Example 2

Preparation of mRNA (1) Construction of Vector DNA

Using pGEM-luc vector (5 ng, manufactured by Promega) as a template, a primer (Luc T7-F3-Kpn) having a base sequence depicted in SEQ ID; No 1, a primer (Luc T7-R4-Kpn) having a base sequence depicted in SEQ ID; No 2, and KOD plus (manufactured by TOYOBO Co.) PCR was performed at 97° C., 15 sec, 55° C., 30 sec and 68° C., 120 sec for 30 cycles. DNA fragment was purified by ethanol precipitation, and digested with KpnI.

Separately, $pT_NT$ vector (manufactured by Promega) was digested with KpnI. These reaction solutions were separated by agarose gel electrophoresis, and using a Gen Elute Gel Purification Kit (manufactured by SIGMA), DNA fragment was purified.

Using Ligation High (manufactured by TOYOBO Co.), a DNA fragment obtained from the above-mentioned pGEM-luc vector and a DNA fragment obtained from the above-mentioned $pT_NT$ vector were ligated and Escherichia coli DH5α (manufactured by TOYOBO Co.) was transformed. Plasmid DNA was prepared from the transformed Escherichia coli by alkali-SDS methods, and subjected to a sequencing reaction (96° C. 10 sec, 50° C. 5 sec, 60° C. 4 min, 30 cycles) using a primer (T7 promoter) having a base sequence depicted in SEQ ID; No 3 and Big Dye Terminator Cycle Sequencing FS (manufactured by Applied Biosystems). This reaction solution was applied to ABI PRISM 310 Genetic Analyzer (manufactured by Applied Biosystems), and base sequence was analyzed. A plasmid having a start codon of luciferase gene inserted into the downstream of $pT_NT$ vector-derived 5'-β-globin leader sequence was named as $pT_NT$-Luc.

(2) In Vitro Transcription Reaction $pT_NT$-Luc prepared in the above-mentioned (1) was digested with BamHI, and purified by phenol-chloroform extraction and ethanol precipitation. Using this as a template, in vitro transcription reaction was carried out. The transcription reaction solution used had the following composition.

[Composition of Transcription Reaction Solution]
  80 mM HEPES-KOH (pH 7.4)
  24 mM magnesium acetate
  40 mM DTT
  7.5 mM NTPs (ATP, GTP, UTP, CTP)
  2 mM spemidine
  1 U/µL RNase inhibitor (derived from human placenta)
  1 U/µL T7 RNA polymerase
  50 µg/mL $pT_NT$-Luc/BamHI NTPs (manufactured by SIGMA), RNase inhibitor (manufactured by TAKARA SHUZO Co.) and T7 RNA polymerase (manufactured by Promega) were respectively used. As a reaction device, low temperature dry block MG-1000 (manufactured by TOKYO RIKAKIKAI Co.) was used. The transcription reaction was carried out at 37° C. for 4 hr, and the amount of the reaction solution was 20 µL.

(3) Purification of Exogenous mRNA

After the completion of the transcription reaction, 1 U RQ1 RNase free DNase (manufactured by Promega) was added to the reaction solution (20 µL) of the above-mentioned (2). The mixture was incubated at 37° C. for 15 min to digest the template DNA. Protein was removed by phenol-chloroform extraction, and potassium acetate was added to the final concentration of 0.3 M to perform ethanol precipitation. The obtained precipitate was dissolved in 100 μL of distilled water and applied to Nick Column (manufactured by Amersham Biosciences) and eluted with distilled water (400 μL). The eluted fraction was recovered, potassium acetate was added to the final concentration of 0.3 M, and ethanol precipitation was conducted. For quantification of the synthesized exogenous mRNA, absorbance at 260 nm was measured. As a result, about 60 μg of exogenous mRNA was synthesized by 20 μL scale reaction.

Experimental Example 3

Cell-Free Protein Synthesis Using mRNA Obtained in Reference Example 2

A reaction solution having the same composition as in Experimental Example 1 was prepared in the same manner as in Example 1 except that mRNA obtained in the above-mentioned Reference Example 2 was used as a template and the extract solution prepared in Example 1 and concentrated in such a manner that the absorbance at 280 nm became 35 was used as an extract solution, cell-free protein synthesis reaction and quantification of synthesized luciferase were performed.

As a result, the amount of luciferase synthesis 3 hr after synthesis reaction was 218 ng/mL, which was about 2.5 times the amount when control mRNA (manufactured by Promega) was used as a template, which was 89 ng/mL.

Experimental Example 4

Effect of the Amount of Each Component Added in Cell-Free Protein Synthesis

The effect of the amount of each component added in the cell-free protein synthesis reaction was examined using a sample obtained by concentrating the extract solution prepared by a method similar to Example 1 so that the absorbance thereof at 280 nm would become 35. As a result, the optimal composition of the obtained reaction solution was as follows.

[Composition of the Reaction Solution]
  50 (v/v) % yeast extract solution
  25 mM HEPES-KOH (pH 7.0)
  50 mM potassium acetate
  2 mM magnesium acetate
  1 mM DTT
  10 (v/v) % glycerol
  0.5 mM ATP
  0.1 mM GTP
  25 mM creatine phosphate
  200 μg/mL creatine kinase
  40 μM amino acid (20 kinds)
  1 U/μL RNase inhibitor (derived from human placenta)
  200 μg/mL tRNA (derived from yeast)
  80 μg/mL mRNA Using a reaction solution having such optimal composition and in the same manner as in Experimental Example 1, luciferase synthesis reaction and quantification were conducted in the same manner as in Example 1. As a result, 580 ng/mL of luciferase was synthesized in 3 hr from the start of the synthesis reaction.

Experimental Example 5

Cell-Free Synthesis of Protein by Dialysis Method

Using a sample obtained by concentrating the extract solution prepared by a method similar to Example 1 so that the absorbance thereof at 280 nm would become 35, a reaction solution having the composition of the above-mentioned Experimental Example 4 was prepared. The mixture was subjected to cell-free protein synthesis by a dialysis method. As the dialysis membrane, Slide-A-Lyzer (exclusion molecular weight: 10,000 or below, manufactured by PIERCE) was used and an outer solution (1.1 mL) for dialysis having the following composition was used.

[Composition of Outer Solution for Dialysis]
  25 mM HEPES-KOH (pH 7.0)
  50 mM potassium acetate
  2 mM magnesium acetate
  1 mM DTT
  10 (v/v) % glycerol
  0.5 mM ATP
  0.1 mM GTP
  25 mM creatine phosphate
  40 μM amino acid (20 kinds)

A cell-free protein synthesis reaction and quantification of synthesized luciferase were performed in the same manner as in Experimental Example 1.

Figure 3:
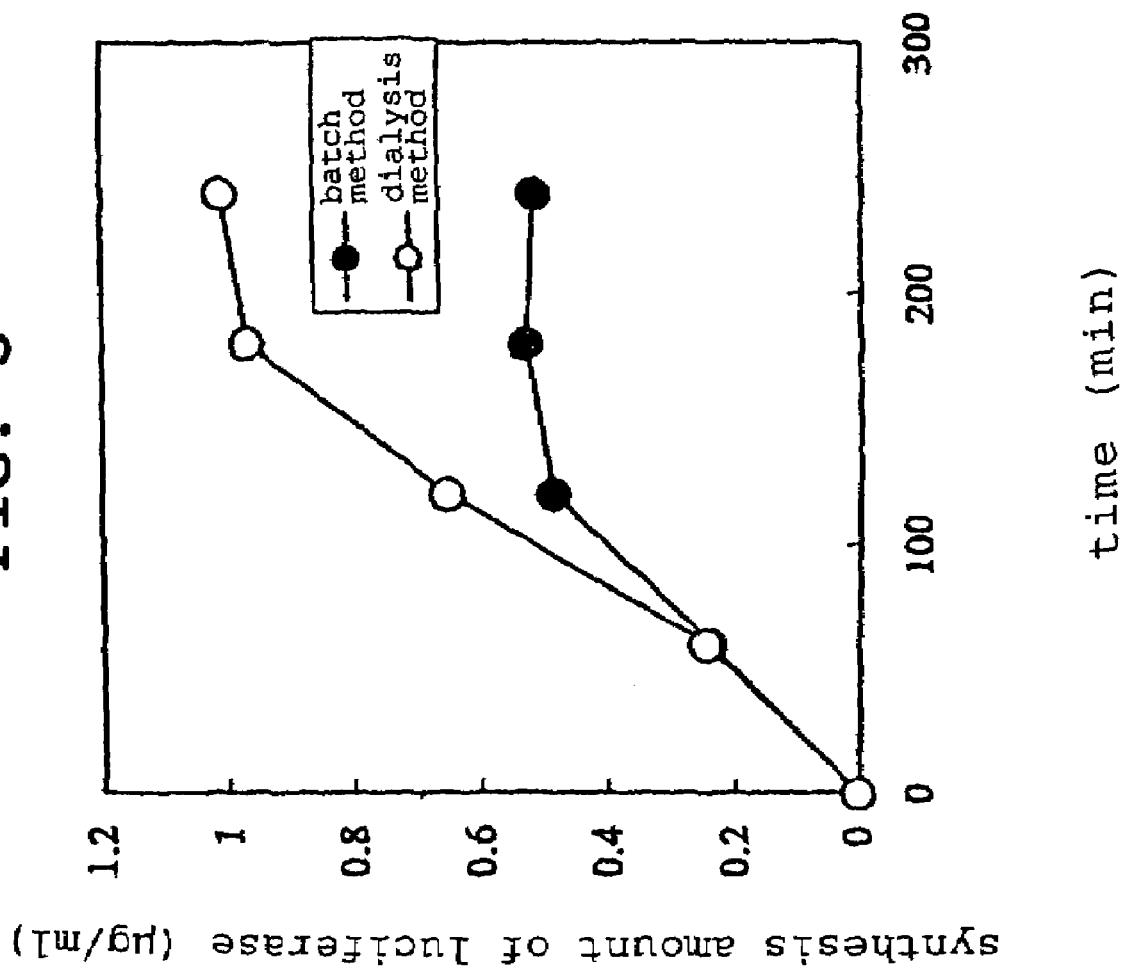
FIG. 3 is a graph showing the comparison of synthesis amounts of luciferase relative to reaction time, between a cell-free protein synthesis reaction by a dialysis method and that by a batch method.

FIG. 3 is a graph showing the comparison of synthesis amounts of luciferase relative to reaction time, between a cell-free protein synthesis reaction by a dialysis method and that by a batch method (results of Experimental Example 4). In FIG. 3, the axis of ordinate shows the amount of synthesized luciferase (μg/mL) and the axis of abscissa shows reaction time (min). As shown in FIG. 3, 1.0 μg/mL of luciferase was synthesized by the dialysis method, which was about 1.7 times the synthesis amount when the dialysis was not performed.

INDUSTRIAL APPLICABILITY

As is clear from the above explanation, according to the present invention, a preparation method of a yeast extract solution for cell-free protein synthesis, which solution is easy to prepare and is capable of synthesizing a higher amount of protein than by conventional yeast extract solutions, the yeast extract solution, a cell-free synthesis method of protein, which uses the yeast extract solution, and a kit for cell-free protein synthesis containing the yeast extract solution can be provided.

This application is based on patent application No. 001317/2003 filed in Japan, the contents of which are incorporated hereinto by reference.

Free Text of Sequence Listing
SEQ ID; No 1
  Primer Luc T7-F3-Kpn
SEQ ID; No 2
  Primer Luc T7-R4-Kpn
SEQ ID; No 3
  Primer T7 promoter

What is claimed is:

1. A method for preparing a yeast-derived extract solution for cell-free protein synthesis, said method comprising:
freezing yeast cells to obtain frozen yeast cells;
rupturing said frozen yeast cells to obtain ruptured frozen yeast cells;
extracting said ruptured frozen yeast cells with a buffered solution for extraction containing a protease inhibitor and diothiothreitol to obtain a liquid containing a yeast-derived extract;
removing residue of the yeast cells and intracellular components having a molecular weight of not more than 5,000 from said liquid containing the yeast extract to obtain an extract solution containing yeast-derived extract; and
concentrating said extract solution containing the yeast-derived extract to obtain the yeast extract solution for cell-free protein synthesis, wherein said concentrated yeast extract solution for cell-free protein synthesis has an absorbance at 280 nm of 35-100.

2. The method of claim 1, wherein the yeast cells are frozen with liquid nitrogen.

3. The method of claim 1, wherein the yeast cells are ruptured by mashing in a mortar with a pestle.

4. The method of claim 1, wherein said yeast-derived extract solution for cell-free protein synthesis contains the yeast-derived extract in a proportion of 1 mg/mL-200 mg/mL in a protein concentration, together with 1 mM-500 mM of potassium acetate, 0.01 mM-10 mM of magnesium acetate, 0.01 mM-10 mM of dithiothreitol, 1 µM-50 mM of phenylmethanesulfonyl fluoride and 5 mM-200 mM of 4-(2-hydroxyethyl)-1-piperazineethanesulfonic acid (HEPES)-KOH at a pH of 6-8.

* * * * *

SEQUENCE LISTING

<160> NUMBER OF SEQ ID NOS: 3

<210> SEQ ID NO 1
<211> LENGTH: 30
<212> TYPE: DNA
<213> ORGANISM: Artificial Sequence
<220> FEATURE:
<223> OTHER INFORMATION: Luc T7-F3-Kpn

<400> SEQUENCE: 1
ggggtaccat ggaagacgcc aaaaacataa                30

<210> SEQ ID NO 2
<211> LENGTH: 29
<212> TYPE: DNA
<213> ORGANISM: Artificial Sequence
<220> FEATURE:
<223> OTHER INFORMATION: Luc T7-R4-Kpn

<400> SEQUENCE: 2
ggggtacctt acaatttgga ctttccgcc                 29

<210> SEQ ID NO 3
<211> LENGTH: 20
<212> TYPE: DNA
<213> ORGANISM: Artificial Sequence
<220> FEATURE:
<223> OTHER INFORMATION: T7 promoter

<400> SEQUENCE: 3
taatacgact cactataggc                           20